United States Patent [19]

Brill

[11] Patent Number: 5,268,464
[45] Date of Patent: Dec. 7, 1993

[54] PROCESS FOR THE PREPARATION OF NUCLEOSIDES

[75] Inventor: Wolfgang K. D. Brill, Freiburg-Waltershofen, Fed. Rep. of Germany

[73] Assignee: Ciba-Geigy Corporation, Ardsley, N.Y.

[21] Appl. No.: 31,455

[22] Filed: Mar. 15, 1993

[30] Foreign Application Priority Data

Mar. 23, 1992 [CH] Switzerland .............. 906/92

[51] Int. Cl.$^5$ .................. C07H 21/00; C07H 21/02; C07H 19/04; C07H 19/056
[52] U.S. Cl. .................. 536/25.3; 536/25.31; 536/25.33; 536/26.21; 536/26.71; 536/28.4; 536/28.54; 536/28.6
[58] Field of Search .............. 536/25.3, 25.31, 25.33, 536/26.21, 26.71, 28.4, 28.54, 28.6

[56] References Cited

U.S. PATENT DOCUMENTS

| | | | |
|---|---|---|---|
| 4,373,071 | 2/1983 | Itakura et al. | 536/25.33 |
| 4,458,066 | 7/1984 | Caruthers et al. | 536/25.34 |
| 4,667,025 | 5/1987 | Miyoshi et al. | 536/25.31 |
| 4,672,110 | 6/1987 | Letsinger | 536/25.31 |
| 4,818,681 | 4/1989 | Dattagupta | 536/24.31 |
| 4,950,745 | 8/1990 | Ishido et al. | 536/25.31 |
| 5,026,838 | 6/1991 | Nojiri et al. | 536/25.31 |
| 5,042,524 | 9/1991 | Andrus et al. | 536/25.31 |
| 5,134,228 | 7/1992 | Takaku | 536/25.3 |

FOREIGN PATENT DOCUMENTS

| | | | |
|---|---|---|---|
| 0040099 | 11/1981 | European Pat. Off. | 536/25.31 |
| 0271332 | 8/1989 | Fed. Rep. of Germany | 536/25.31 |
| 0809866 | 3/1982 | U.S.S.R. | 536/25.31 |
| 0002533 | 2/1992 | World Int. Prop. O. | 536/25.31 |

*Primary Examiner*—Herbert J. Lilling
*Attorney, Agent, or Firm*—Kevin T. Mansfield; George R. Dohmann

[57] ABSTRACT

A process for the preparation of natural or synthetic nucleosides, nucleoside analogs or oligonucleotides from at least two such nucleosides and/or nucleoside analogs whose basic molecule contains an unsubstituted or substituted radical of a nucleic base B and a protected hydroxyl group of formula $R_1$—O—, wherein $R_1$ is a protective group, or which are linked to the oxygen atom of a hydroxyl group direct or to a solid support through a linking group, from nucleoside monomers or from oligonucleotides to the basic molecule of which, in addition to said radicals, a group of formula I, Ia or Ib

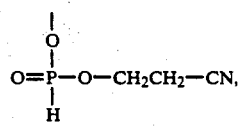

(I)

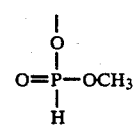

(Ia)

or

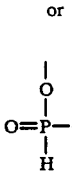

(Ib)

is attached, by converting the group of formula I, Ia or Ib into a hydroxyl group —OH by reacting the nucleosides or oligonucleotides, in the absence or presence of an inert organic solvent, with an excess of an aliphatic, cycloaliphatic araliphatic or aromatic alcohol containing 1 to 30 carbon atoms, a polyol containing 2 to 50 carbon atoms or a polymeric polyol, in the presence of at least a catalytic amount of an inorganic base or of an organic nitrogen base, which base has a pK value of 4 to 10.

36 Claims, No Drawings

PROCESS FOR THE PREPARATION OF NUCLEOSIDES

The present invention relates to a process for the preparation of natural or synthetic nucleosides, nucleoside analogs or oligonucleotides with at least two identical or different such nucleoside monomers.

Many nucleotides of defined sequence are currently synthesised by the phosphite triester process. In this process, an oligonucleotide is synthesised from its 3'-terminal stepwise to the 5' direction. The synthesis begins with the linkage of the 3'-terminal nucleotide which carries a protective group at its 5'-hydroxyl group and, if necessary, at its nucleoside base, to a chemically inert solid phase. The 5'-hydroxy protective group is subsequently removed. The reaction with a 3'-phosphoramidite of an appropriately protected nucleoside results in the formation of the internucleotide linkage. The resulting phosphite triester is thereafter oxidised to the desired internucleotide linkage. The next synthesis cycle can then be initiated with the removal of the 5'-terminal protective group of the dinucleonide immobilised on the solid phase. The synthesis cycles are repeated until the oligonucleotide bonded to the solid phase is obtained. The synthesis ends with the removal of the protective groups at the nucleoside bases, hydroxy groups and the internucleotide bonds (Caruthers, M. H., Science 230:281-285, 1985). Depending on the type of phosphoramidite, the nucleoside or oligonucelotide used typically contains the groups of formulae

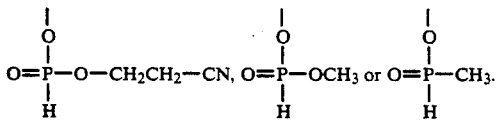

The problem with this method of synthesis is the condensation reaction between the phosphoramidite and the free hydroxyl group of the nucleosides or oligonucleotides immobilised on the solid phase. In this reaction step the exclusion of water must be rigorously ensured. Even the use of absolute solvents does not completely ensure the exclusion of water. For this reason, in the coupling step of the solid phase oligonucleotide synthesis substantial amounts of nucleoside phosphoramidite are converted into nucleoside phosphoramidite hydrolysate, for example nucleoside cyanoethyl hydrogenphosphonate. This last mentioned compound does not participate in the coupling reaction. Nevertheless, to achieve high coupling yields it is necessary to use large excesses of phosphoramidites. In state-of-the-art DNA synthesising machines up to 2- to 20-fold excesses of nucleoside phosphoramidite are used relative to the amount of hydroxy component immobilised on the solid phase. The maximum yield of internucleotide linkage is 20% relative to the phosphoramidite used. A minimum of 80% of the nucleosides used is discarded as nucleoside phosphoramidite hydrolysate. This problem cannot be entirely overcome by making improvements to the apparatus employed, e.g. special metering devices (q.v. Chemische Rundschau Nr. 37, Seite 11 (1992).

Böhringer, (Böhringer, M. P., doctoral thesis of the Eidgenössische Technische Hochschule, ETH No. 9377, 1991) reacts the hydrolysate of a methyl phosphoramidite of a nucleoside analog with sodium hydroxide solution to the nucleoside analog containing a free hydroxy group. However, under the conditions employed by him, the protective groups of the nucleoside bases are removed.

The processes described by Predvoditelev et al. (Predvoditelev, D. A., Tyuganova, M. A., Nifant'ev, E. E., Rogovin, Z. A., Zh. Prikl. Khim. 40:171-177, 1967), Nifnt'ev et al. (Nifnt'ev, E. E., Predvoditelev, D. A., Fursenko, I. V., Zh. Obsh. Khim. 51:2435-2441, 1981), Troev and Simeonov (Troev, K., Simeonov, M., Phosphorus and Sulfur 19:363-367, 1984) and Westheimer et al. (Westheimer, F. H., Huang, S., Covitz, F., J. Am. Chem. Soc. 110:181-185, 1988) for the transesterification of non-nucleotide dialkylphosphites all have the disadvantage that, when applied to protected nucleosides, the protective groups of the nucleic acid bases are easily removed. In these processes the high temperature required is an impediment to their wide use because of thermal decomposition reactions, for example the thermal removal of protective groups, especially detritylation.

Another process is the Lewis acid-catalysed transesterification with tetrakis benzyloxytitanium, which is carried out at 40° C. over 72 hours with moderate yields and in which the sensitivity to hydrolysis of the titanate is particularly disadvantageous (Froneman, M., Modro, T. A., Synthesis 201-204, 1991).

Surprisingly, the present invention provides a process for converting nucleoside hydrogenphosphonates or hydrogenphosphinates into nucleosides which carry a free hydroxyl group at that position in which the hydrogenphosphonate or hydrogenphosphinate function was located. In the inventive process, the hydrogenphosphonate or hydrogenphosphinate group is transferred to an alcohol in high selectivity relative to other acyl protective groups. The selectivity of the removal can be so great that, even after several days under the given reaction conditions, the protective groups of the nucleoside bases are not removed. Furthermore, high yields are obtained in this process. The novel process makes it possible for the first time to recover the necleoside excesses occurring in the nucleotide coupling by the standard phosphite triester process during the routine continuous operation of the manual or automated oligonucleotide synthesis.

The invention provides in particular a process for the preparation of natural or synthetic nucleosides, nucleoside analogs or oligonucleotides from at least two such nucleosides and/or nucleoside analogs whose basic molecule contains an unsubstituted or substituted radical of a nucleic base B and a protected hydroxyl group of formula R₁—O—, wherein R₁ is a protective group, or which are linked to the oxygen atom of a hydroxyl group direct or to a solid support through a linking group, from nucleoside monomers or from oligonucleotides to the basic molecule of which, in addition to said radicals, a group of formula I, Ia or Ib

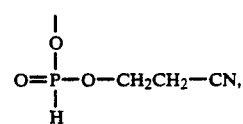
(I)

-continued

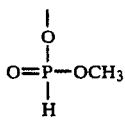
(Ia)

or

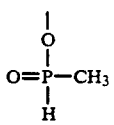
(Ib)

is attached, by converting the group of formula I, Ia or Ib into a hydroxyl group —OH by reacting the nucleosides or oligonucleotides, in the absence or presence of an inert organic solvent, with an excess of an aliphatic, cycloaliphatic, araliphatic or aromatic alcohol containing 1 to 30 carbon atoms, a polyol containing 2 to 50 carbon atoms or a polymeric polyol, in the presence of at least a catalytic amount of an inorganic base or of an organic nitrogen base, which base has a pK value of 4 to 10.

The groups of formulae I, Ia and Ib can be attached in the 3'- or 5'-positions of the nucleosides or oligonucleotides, while the $R_1O$— group or the solid support is attached in the 5'- or 3'-positions. The group of formula I is preferably attached in the 5'-position, the group of formula Ib in the 3'-position, and the group of formula Ia in the 3'- or 5'-position.

A great number of nucleosides, nucleoside analogs or oligonucleotides carrying preferably a secondary OH group for the attachment of the nucleotide linkage and suitable for use in the process of this invention are known and described e.g. in Townsend (Townsend, L. B., Hrsg., Chemistry of Nucleosides and Nucleotides 1, Plenum Press, New York, 1988), or can be prepared by known methods. Quite generally they may be an open-chain C-structure interrupted by —O— or —S— or a carbacyclic or an O— or S-heterocyclic structure with a nucleic acid base B.

The open-chain carbon structure may typically contain 3 to 12, preferably 3 to 6, carbon atoms. The carbacylic and heterocyclic structures may be monocyclic ring systems containing 3 to 12, preferably 3 to 8 and, most preferably, 4 or 5, ring carbon atoms. They may also be bicyclic or tricyclic systems containing 5 to 16, preferably 8 to 16, carbon atoms. The structures may contain further substituents, typically protected OH groups.

If the nucleic base B is a purine residue or an analog thereof it may be a radical of formula II, IIa, IIb, IIc, IId or IIe

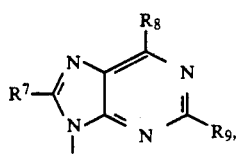
(II)

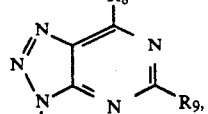
(IIa)

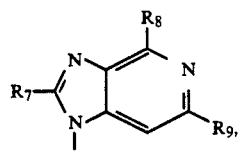
(IIb)

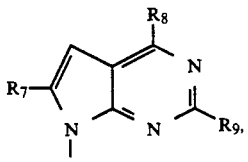
(IIc)

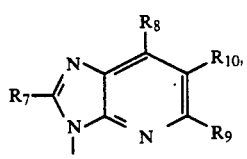
(IId)

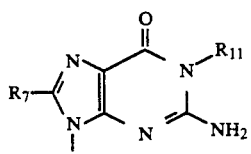
(IIe)

wherein $R_7$ is H, Cl, Br, $NH_2$ or OH, and $R_8$, $R_9$ and $R_{10}$ are each independently of one another H, OH, SH, $NH_2$, $NHNH_2$, NHOH, NHOalkyl of 1 to 12 carbon atoms, F, Cl, Br, alkyl or hydroxyalkyl or aminoalkyl or alkoxy or alkylthio of 1 to 12 carbon atoms, which hydroxyl and amino groups may be unsubstituted or substituted by a protective group, or phenyl, benzyl, primary amino of 1 to 20 carbon atoms or secondary amino of 2 to 30 carbon atoms, and $R_{11}$ is H or $C_1$-$C_4$alkyl.

Primary amino preferably contains 1 to 12 and, most preferably, 1 to 6, carbon atoms, and secondary amino preferably contains 2 to 12 and, most preferably, 2 to 6, carbon atoms.

Representative examples of alkyl, alkoxy, alkylthio, hydroxyalkyl and aminoalkyl, which preferably contain 1 to 6 carbon atoms, are methyl, ethyl and the isomers of propyl, butyl, pentyl, hexyl, heptyl, octyl, nonyl, decyl, undecyl and dodecyl, as well as corresponding alkoxy, alkylthio, hydroxyalkyl and aminoalkyl radicals. Alkyl, alkoxy, alkylthio, hydroxyalkyl and aminoalkyl most preferably contain 1 to 4 carbon atoms. Preferred alkyl, alkoxy, alkylthio, hydroxyalkyl and aminoalkyl radicals are methyl, ethyl, n- and isopropyl, n-, iso- and tert-butyl, methoxy, ethoxy, methylthio and ethylthio, aminomethyl, aminoethyl, hydroxymethyl and hydroxyethyl.

Primary amino and secondary amino may typically be radicals of formula $R_{14}R_{15}N$, wherein $R_{14}$ is H or independently has the meaning of $R_{15}$, and $R_{15}$ is alkyl, aminoalkyl or hydroxyalkyl of 1 to 20, preferably 1 to 12 and, most preferably, 1 to 6, carbon atoms; carboxyalkyl or carbalkoxyalkyl, the carbalkoxy group containing 2 to 8 carbon atoms and the alkyl moiety containing 1 to 6, preferably 1 to 4, carbon atoms; alkenyl of 2 to 20, preferably 2 to 12 and, most preferably, 2 to 6, carbon atoms; phenyl, mono- or di-($C_1$-$C_4$-alkylphenyl or $C_1$-$C_4$lkoxy)phenyl, benzyl, mono- or di-($C_1$-$C_4$alkylbenzyl or $C_1$-$C_4$-alkoxy)benzyl; or 1,2-, 1,3- or 1,4-imidazolyl-$C_1$-$C_6$alkyl, or $R_{14}$ and $R_{15}$, taken together, are tetra- or pentamethylene, 3-oxa-1,5-pentylene, —$CH_2$—$NR_{16}$—$CH_2CH_2$— or —$CH_2CH_2$—$NR_{16}$—$CH_2CH_2$—, wherein $R_{16}$ is H or $C_1$-$C_4$alkyl. The amino group of aminoalkyl may be substituted by one or two $C_1$-$C_4$alkyl or $C_1$-$C_4$hydroxyalkyl groups. The hydroxyl group of hydroxyalkyl can be etherified with $C_1$-$C_4$alkyl.

Examples of alkyl are cited above. Representative examples of aminoalkyl are aminomethyl, aminoethyl, 1-aminoprop-2-yl or -3-yl, 1-amino-but-2-yl or -3-yl or -4-yl, N-methyl- or N,N-dimethyl- or N-ethyl- or N,N-diethyl- or N-2-hydroxyethyl- or N,N-di-2-hydroxyethylaminomethyl or -aminoethyl or -aminopropyl or -aminobutyl. Exemplary hydroxyalkyl groups are hydroxymethyl, 1-hydroxy-eth-2-yl, 1-hydroxy-prop-2- or -3-yl, 1-hydroxy-but-2-yl, -3-yl or -4-yl. Exemplary carboxyalkyl groups are carboxymethyl, carboxyethyl, carboxypropyl and carboxybutyl; and exemplary carbalkoxyalkyl groups are said carbalkoxyalkyl groups which are esterified with methyl or ethyl. Alkenyl is typically allyl, but-1-en-3-yl or -4-yl, pent-3- or 4-en-1-yl or -2-yl, hex-3- or -4- or -5-en-1-yl or -2-yl. Typical examples of alkylphenyl, alkoxyphenyl and alkylbenzyl are methylphenyl, dimethylphenyl, ethylphenyl, diethylphenyl, methylbenzyl, dimethylbenzyl, ethylbenzyl, diethylbenzyl, methoxyphenyl, dimethoxyphenyl, ethoxyphenyl, diethoxyphenyl, methoxybenzyl, dimethoxybenzyl, ethoxybenzyl, diethoxybenzyl. Imidazolylalkyl in which the alkyl moiety preferably contains 2 to 4 carbon atoms is typically 1,2-, 1,3- or 1,4-imidazolylethyl or -n-propyl or -n-butyl. $R_{16}$ is preferably H, methyl or ethyl.

Preferred examples of primary amino and secondary amino are methylamino, ethylamino, dimethylamino, diethylamino, allylamino, mono- or di-(1-hydroxy-eth-2-yl)amino, phenylamino and benzylamino, acetylamino and benzoylamino.

In a preferred embodiment of the invention, $R_7$ is hydrogen. In another preferred embodiment of the invention, $R_{10}$ is hydrogen. In a further preferred embodiment of the invention, $R_8$ and $R_9$ are each independently of the other H, F, Cl, Br, OH, SH, $NH_2$, NHOH, $NHNH_2$, methylamino, dimethylamino, benzoylamino, methoxy, ethoxy and methylthio.

Representative examples of analogs of the purine series are, in addition to purine, adenine, N-methyladenine, N-benzyladenine, 2-methyladenine, 2-methylthioadenine, 2-aminoadenine, 3-carbaadenine, 7-carbaadenine, 1-carbaadenine, 6-hydroxypurine, 2-amino-6-chloropurine, 2-amino-6-methylthiopurine, 2-amino-6-hydroxypurine, 3-carba-6-chloropurine, guanine, 2-methylguanine. Adenine, 2-aminoadenine and guanine are especially preferred.

If the nucleic acid base is an analogous pyrimidine radical, said radical is preferably a uracil, thymine and cytosine radical of formulae III, IIIa and IIIb.

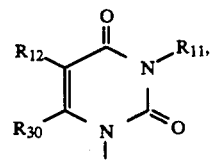

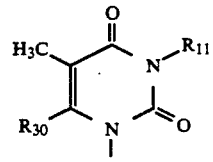

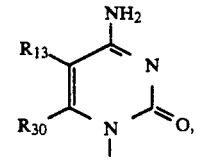

wherein $R_{11}$ is H or $C_1$-$C_4$alkyl, and $R_{12}$, $R_{13}$ and $R_{30}$ each independently of the other have the meanings previously given in respect of $R_8$, including the preferred meanings, and the hydrogen atoms of the $NH_2$ group in formula IIIb may be substituted by $C_1$-$C_6$alkyl or benzoyl, as well as the dihydro derivatives of the radicals of formulae III, IIIa nd IIIb. Preferably $R_{12}$ is H, $C_1$-$C_6$alkyl or hydroxyalkyl, F, Cl, Br, $NH_2$, benzoylamino, mono- or di-$C_1$-$C_6$alkylamino, and $R_{13}$ is preferably H, $C_1$-$C_6$alkyl or $C_1$-$C_6$alkoxy or $C_1$-$C_6$hydroxyalkyl, F, Cl, Br, $NH_2$, benzoylamino, mono- or di-$C_1$-$C_6$alkylamino.

$R_{11}$ is preferably H or methyl. $R_{12}$ is preferably H, F, Cl, Br, $NH_2$, $NHCH_3$, $N(CH_3)_2$ or $C_1$-$C_4$alkyl. $R_{13}$ is preferably H, $C_1$-$C_4$alkyl, more particularly methyl, or $NH_2$, $NHCH_3$ or $(CH_3)_2N$.

Representative examples of pyrimidine analogs are uracil, thymine, cytosine, 5-fluorouracil, 5-chlorouracil, 5-bromouracil, dihydrouracil, pseudouracil, 1-methylpseudouracil, 5-methyluracil, 3-methylcytosine and 5-methylcytosine.

Within the scope of this invention, protective groups will be understood as meaning the protective groups commonly known in chemistry. Typical examples of such protective groups are: $C_1$-$C_8$alkyl; mono- or bicyclic $C_7$-$C_{12}$aralkyl; mono- or bicyclic $C_7$-$C_{12}$aralkoxy; mono- or bicyclic $C_7$-$C_{12}$haloaralkyl; diphenylmethyl; diphenylmethyl substituted by 1 to 4 methyl or methoxy groups; triphenylmethyl; triphenylmethyl substituted by 1 to 6 methyl or methoxy groups or by 1 to 3 tert-butyl groups; xanthenyl substituted by phenyl or naphthyl; —Si($R_4$)($R_5$)($R_6$), wherein ($R_4$)($R_5$) and ($R_6$) are each independently of one another $C_1$-$C_{20}$alkyl, benzyl or phenyl; R—C(O)—, wherein R is $C_1$-$C_6$alkyl, benzyl, benzyl substituted by methyl, methoxy or halogen, $C_1$-$C_{12}$alkoxy, $C_1$-$C_{12}$alkoxy substituted by fluorene, phenoxy, phenoxy substituted by methyl, methoxy or halogen, benzyloxy or benzyloxy substituted by methyl, methoxy or halogen; $R_{17}$—$SO_2$—, wherein $R_{17}$ is $C_1$-$C_{12}$alkyl, $C_5$-$C_6$cycloalkyl, phenyl, phenyl substituted by $C_1$-$C_{12}$alkyl or halogen, benzyl or benzyl substituted by $C_1$-$C_{12}$alkyl or halogen; $C_1$-$C_{12}$alkoxyacetyl or phenoxyacetyl which is unsubstituted or substituted by one or more than one identical or different member selected from the group consisting of linear or branched $C_1$-$C_6$alkyl, $C_1$-$C_6$haloalkyl, halogen, $C_1$-$C_6$alkoxy, $C_1$-$C_6$alkylthio, nitro and cyano.

Typical examples of $C_1$-$C_8$alkyl are methyl, ethyl, n- and isopropyl, n-, iso- and tert-butyl; typical examples of monocyclic $C_7$-$C_{12}$aralkyl are benzyl, methylbenzyl, dimethylbenzyl; typical examples of mono- or bicyclic $C_7$-$C_{12}$aralkoxy are methoxybenzyl, dimethoxybenzyl; mono- or bicyclic $C_7$-$C_{12}$haloalkyl is exemplified by bromobenzyl; typical examples of substituted diphenylmethyl are di(methylphenyl)methyl, di(dimethylphenyl)methyl, di(methoxyphenyl)methyl and di(dimethoxyphenyl)methyl; typical examples of substituted triphenylmethyl are tri(methylphenyl)methyl, tri(dimethylphenyl)methyl, tri(methoxyphenyl)methyl, tri(dimethoxyphenyl)methyl, monomethoxytrityl, dimethoxytrityl and tris-p-tert-butylphenylmethyl; typical examples of silyl groups are triphenylsilyl, trimethylsilyl, triethylsilyl, tri-n-propylsilyl, isopropyldimethylsilyl, tert-butyldimethylsilyl, tert-butyldiphenylsilyl, n-octyldimethylsilyl, (1,1,2,2-tetramethylethyl)dimethylsilyl; the R—C(O)— group is exemplified by acetyl, trifluoroacetyl, propanoyl, butanoyl, pentanoyl, hexanoyl, benzoyl, methylbenzoyl, methoxybenzoyl, chlorobenzoyl, brombenzoyl, methoxy-, ethoxycarbonyl, n- or isopropoxycarbonyl or n-, iso- or tert-butoxycarbonyl, or phenoxycarbonyl, benzyloxycarbonyl, methyl- or methoxy- or chlorophenoxycarbonyl or chlorobenzyloxycarbonyl or 9-fluorenylmethoxycarbonyl; and typical examples of the $R_{17}$—$SO_2$— group are methylphenylsulfonyl, ethylphenylsulfonyl, propylphenylsulfonyl, butylphenylsulfonyl, phenylphenylsulfonyl, benzylphenylsulfonyl, p-bromophenylsulfonyl, p-methoxyphenylsulfonyl and p-methylphenylsulfonyl; and typical examples of alkoxyacetyl and phenoxyacetyl are methoxyacetyl, ethoxyacetyl, phenoxyacetyl, (p-methylphenoxy)acetyl, (p-tert-butylphenoxy)acetyl. Amidine protective groups are also frequently used in nucleic acid bases.

The nucleosides and oligonucleotides can be covalently bonded to a solid support through a linking group. Suitable supports are typically silica gels, controlled pore glass, polystyrene, polyacrylamide, polyurethanes, polyolefins, melamine, polyamides, polyesters, polyethers, polyalcohols, cyclodextrin, cellulose and etherified or acylated cellulose derivatives, glycogen, starch, chitine and chitosane. Depending on the choice of support, the linking group can be derived from dicarboxylic acids. diurethanes or alkoxysilylurethanes.

The process of this invention can be carried out in the presence of an additional solvent. Without an additional solvent, the alcohol, polyol or the polymeric polyol used in the novel process, provided it is liquid, is the solvent. Suitable additional solvents are those solvents which do not compete in the reaction batch with the alcohol, the polyol or the polymeric polyol. They can be used alone or as a mixture of at least two solvents. In the case of polyols it is also possible to use solvents or solubilisers which make the alcohol groups available to the process by the swelling of the polyol. Representative examples of such solvents are those selected from the group consisting of ethers, halogenated hydrocarbons, carboxamides, lactams, sulfoxides, sulfones, aromatic hydrocarbons, nitriles, aliphatic and cycloaliphatic hydrocarbons, preferably ethers, halogenated hydrocarbons, nitriles, carboxamides and lactams. Solubilisers within the scope of this invention may conveniently be salts, typically ammonium acetates and ammonium hydrogencarbonates.

Particularly suitable ethers are dibutyl ether, tetrahydrofuran, dioxane, ethylene glycol diethyl and dimethyl ether, diethylene glycol dimethyl ether, diethylene glycol diethyl ether or triethylene glycol dimethyl ether, preferably tetrahydrofuran, methyl-tertiarybutylether, dibutylether, diisopropylether or dioxane. Particularly suitable halogenated hydrocarbons are methylene chloride, chloroform, 1,2-dichloroethane, 1,1,1-trichloroethane and 1,1,2,2-tetrachloroethane.

Useful amides are N-alkylated or N-dialkylated amides. Typical representatives are N,N-dimethylformamide, N,N-diethylformamide, N,N-dimethylacetamide, tetramethylurea and hexamethylphosphoric triamide.

Preferred lactams are those selected from the group consisting of γ-butyrolactam, ε-caprolactam, N-methylpyrrolidone, N-acetylpyrrolidone and N-methylcaprolactam.

Further suitable solvents within the scope of this invention include dimethyl sulfoxide, dimethyl sulfone, diethyl sulfone, trimethylene sulfone, tetramethylene sulfone, benzene, substituted benzene, preferably chlorobenzene, o-dichlorobenzene, 1,2,4-trichlorobenzene, nitrobenzene, toluene and xylene, acetonitrile, propionitrile, benzonitrile, phenyl acetonitrile, pentane, petroleum ether, hexane, cyclohexane and methyl cyclohexane.

The aliphatic, cycloaliphatic, araliphatic or aromatic alcohol, the polyol or the polymeric polyol used in the process of this invention is referred to hereinafter as as acceptor.

It is convenient to use an alkanol of 1 to 20, preferably 1 to 12 and, most preferably, 1 to 6, carbon atoms, typically a representative of the group consisting of methanol, ethanol, n- and isopropanol, n-, iso- and tert-butanol, pentanol, hexanol, ethylene glycol, diethylene glycol monomethyl and monoethyl ether. A preferred subgroup of the alcohols employed in the process of this invention comprises $C_1$-$C_4$alkanols. It is especially preferred to use methanol.

Also suitable is an alkyl-substituted cycloalkanol containing 5 to 12, preferably 5 to 8, ring carbon atoms, typically selected from the group consisting of cyclopentanol, cyclohexanol, methyl cyclohexanol, cycloheptanol and cyclooctanol.

Exemplary of further suitable acceptors are araliphatic alcohols of 7 to 30, preferably of 7 to 20, carbon atoms, preferably selected from the group consisting of unsubstituted or alkyl- or alkoxy-substituted benzyl alcohol and β-phenylethanol; aromatic alcohols of 6 to 30, preferably of 6 to 12, carbon atoms, preferably selected from the group consisting of phenol and unsubstituted or alkyl- or alkoxy-substituted naphthol; polyols of 2 to 20 carbon atoms, preferably selected from the group consisting of ethylene glycol, propylene glycol, butanediol, pentanediol, hexanediol, cyclohexanediol, dihydroxymethyl cyclohexane, diethylene glycol, triethylene glycol, polyethylene glycol, trimethylolpropane, pentaerythritol, dipentaerythritol, glycerol and saccharides; polymeric polyols, preferably selected from the group consisting of polyvinyl alcohol, polysaccharides and hydroxyalkyl polyacrylates and polymethacrylates. The alkyl and alkoxy substituents preferably contain 1 to 4 carbon atoms.

Within the scope of this invention, saccharide acceptors will be understood as meaning typically mono- and oligosaccharides such as mono-, di-, tri-, tetra- and pentasaccharides. In a preferred embodiment of the invention, the mono- and oligosaccharides are aldoses or ketoses. In a particularly preferred embodiment of the invention, the monosaccharides are aldopentoses, aldohexoses, ketopentoses or ketohexoses.

An aldopentose will typically be D-ribose, D-arabinose, D-xylose or D-lyxose; an aldohexose will typically be D-allose, D-altrose, D-glucose, D-mannose, D-gulose, D-idose, D-galactose or D-talose; a ketopentose will typically be D-ribulose or D-xylulose; a ketohexose will typically be D-psicose, D-fructose, D-sorbose or D-tagatose.

A disaccharide will typically be trehalose, maltose, isomaltose, cellobiose, gentibiose, saccharose or lactose.

A trisaccharide will typically be raffinose.

Polysaccharides are typically cellulose, starch, dextrans, glycogen, fructanes, inuline, mannanes, xylanes and arabinanes.

The inorganic base used in the practice of this invention will preferably be a member selected from the group consisting of basic metal oxide, heavy metal oxide and hydroxide, preferably $SiO_2$ or basic alumina.

Further suitable inorganic bases are those with which the transesterification can be carried out under the conditions of nucleophilic catalysis and which may be components of a buffer system. Preferably they are metal or ammonium fluorides, metal or ammonium aldoximates, ketoximates, hydroxomates, sulfates, phosphates, phosphonates, pyrophosphates, sulfamates, nitrites, nitrates and sulfonates which are soluble in alcohols or the reaction mixture, where metal preferably denotes an alkali metal ion, for example $Na^+$, $Li^+$, $K^+$, $Rb^+$ and $Cs^+$. The metal aldoximates, ketoximates, hydroxomates, sulfamates, sulfonates and phosphonates may contain hydrogen atoms or $C_1$-$C_6$alkyl groups or phenyl groups which are unsubstituted or substituted by halogen, $C_1$-$C_4$alkyl, $C_1$-$C_4$alkoxy, cyano or nitro. The ammonium fluorides are preferably tetra($C_1$-$C_6$alkyl)ammonium fluoride, typically tetra(n-butyl)ammonium fluoride.HF. Further examples are CsF, KF, $CH_3$—C(O)—NH—O$^-$ and $Mg(CF_3CO)_2$. It has been found especially useful to use these nucleophilic bases together with the organic nitrogen bases, advantageously in catalytic amounts.

A particularly useful inorganic nitrogen base is a member selected from the group consisting of aromatic amine, aromatic N-heterocycle and N-$C_1$-$C_4$alkylmorpholine. Typical representatives are imidazole, pyridine, N-methylmorpholine, aniline and o-diaminobenzene, as well as polyvinyl pyridine.

The amount of base used in the inventive process ranges from a catalytic amount to higher amounts, typically up to equivalent amounts or an excess. A catalytic amount within the scope of this invention is in the range from 0.01 to 20% molar, conveniently from 0.1 to 10% molar, preferably from 0.1 to 5% molar, based on 1 mol of nucleoside or oligonucleotide.

In the process of this invention it is preferred to use an excess of not less than 100 molar equivalents and up to 1000 molar equivalents or more of hydroxyl groups of the acceptor per molar equivalent of groups of formula I.

The novel process can be substantially accelerated by the additional use of Lewis acids in amounts of 0.01 to 20% molar, conveniently of 0.1 to 10% molar, preferably of 0.1 to 5% molar, based on 1 mol of nucleoside or oligonucleotide. The high reaction rate obtainable is a substantial advantage. Lewis acids which may suitably be used are metal salts (LiCl), borates or organic metal complexes. The combined use of organic nitrogen base, nucleophilic inorganic base and Lewis acid in the novel process is especially advantageous, as a high selectivity is obtained.

The reaction is conveniently carried out in the temperature range from $-20°$ C. to $+55°$ C., preferably from $15°$ C. to $35°$ C. and, most preferably, at room temperature.

The reaction can conveniently be carried out by adding a nucleoside or oligonucleotide containing radicals of formulae I, Ia and Ib to a solution or mixture of alcohol and a base and allowing the reaction to go to completion. To isolate the desired compounds, any insoluble components can be removed by filtration and the solvent then stripped off. The residue can be purified by conventional methods such as crystallisation or chromatography. In a particularly advantageous embodiment of the novel process, waste solutions from the oligonucleotide synthesis are run direct into a solution or mixture of alcohol and base in order to recover the nucleotide components used in large excess. In this procedure, the waste solution which contains a compound having a radical of formula I, Ia or Ib is routed to the reaction solution or the reaction mixture, such that at the start of the reaction a very large excess of base is present and acid components of such waste solutions can be neutralised. In the course of the reaction the concentration of base decreases and can, if necessary, be replenished. These acid components may preferably be tetrazole or other acids which effect the nucleotide condensation by the phosphite triester process.

For working up the reaction mixtures, the phosphites formed can be treated with customary oxidising agents, for example $I_2$/$H_2O$/pyridine or $S_8$/pyridine, to give the corresponding phosphates or thiophosphates. Upon evaporation of the reaction solutions no more back reaction can then take place, and isolation of the desired products can often be effected by extraction, avoiding chromatographic methods.

It has been found useful to remove the organic nitrogen base, for example imidazole, with a citrate buffer solution (pH c. 3-4) by extraction. An almost complete separation and good phase separation when working up in aqueous medium is thereby achieved.

In a special embodiment of the novel process, cyanoethanol is used as acceptor if the nucleosides or oligonucleotides are attached to a solid support and contain a H-phosphonate or H-phosphinate group and are reacted in the presence of an organic nitrogen base. In this embodiment of the process, a biscyanoethyl phosphite or cyanoethylmethyl phosphinate is formed which is irreversibility reacted with a weakly basic polymeric ion exchanger. The resulting phosphorus compound remains attached by salt formation to the ion exchanger and simultaneously the acrylonitrile formed is held by the ion exchanger. This embodiment of the process avoids a back reaction during the transesterification and in particular the use of large excesses of acceptor can be avoided.

The following Examples illustrate the invention in more detail. The discharge solutions used in Examples 2, 5 and 7 are obtained as follows:

The waste solutions from a solid phase oligonucleotide synthesis reactor are collected according to the process of Gao et al. (Gao, H., Gaffney, B. L., Jones, R. A., Tetrahedron Lett., 1991). The waste solutions, after exit from the reactor, separated according to nucleo-

EXAMPLE 1

Preparation of 5'-dimethoxytritylthymidine from dimethoxytritylthymidin-3'-yl-β-cyanoethylphosphorodiisopropylamidite 270 mg (3.86 mmol) of tetrazole and 9 μl (0.5 mmol) of water are added to a solution of 360 mg (0.48 mmol) of dimethoxytritylthymidin-3'-yl-β-cyanoethylphosphorodiisopropylamidite in 4 ml of acetonitrile. After 5 minutes the hydrolysis of the phosphoroamidite is complete, giving 5'-dimethoxytritylthymidin-3'-cyanoethylhydrogenphosphonate.

To this solution are added 4 ml of methanol and 350 mg of imidazole. After 24 hours the reaction solution is concentrated by evaporation under vacuum. The white to yellowish solid obtained is taken up in 50 ml of dichloromethane.

After extractions with 50 ml of water and 50 ml of sodium hydrogencarbonate, the organic phase is dried over sodium sulfate. The salt and any residual imidazole are removed by filtration. The crude product is concentrated by evaporation and separated by flash chromatography (Still, W. C., Kahn, M. Mitra, A., J. Org. Chem. 43:2923, 1978). The product fractions are combined and concentrated and then taken up in 50 ml of dichloromethane and extracted with 50 ml of 1M triethylammonium hydrogencarbonate. The organic phase is dried over sodium sulfate. The salt is removed by filtration and concentrated to a volume of 1 ml under vacuum. The concentrated product solution is precipitated at room temperature in 50 ml of n-pentane. The precipitation is completed by addition of 200 ml of n-pentane and subsequent cooling to −20° C. The precipitate is isolated by filtration, washed with 50 ml of n-pentane and dried under vacuum over $P_4O_{10}$/KOH. The product obtained is 5'-dimethoxytritylthymidine (5'-dimethoxytritylthymidine: 431 mg, 82.5% of dry solids).

EXAMPLE 2

Preparation of 5'-dimethoxytritylthymidine from the waste solution from an oligonucleotide synthesis reactor 100 ml of a waste solution formed in the reactor in the course of a DNA synthesis and containing 0.24 mmol of 5'-dimethoxytritylthymidin-3'-yl-β-cyanoethylphosphonate are run into 50 ml of a solution of 1 g of imidazole in methanol. Upon conclusion of the reaction, the reaction solution is dried under vacuum to give a white to yellowish solid which is taken up in 100 ml of dichloromethane. After extraction with 3×100 ml of 1M $NaH_2PO_4$/$NaHPO_4$, pH 5.5, the combined aqueous phase is extracted with 50 ml of dichloromethane. The organic phases are combined and then extracted with 2×100 ml of a saturated aqueous solution of sodium hydrogencarbonate. The sodium hydrogencarbonate phase is extracted with 50 ml of dichloromethane and all the organic phases are combined.

The combined organic phase is dried over sodium sulfate. The subsequent recrystallisation from 5 ml of benzene is brought to completion by cooling to −20° C. Then 50 ml of n-hexane are added and the crystallisation is continued for 20 hours at −20° C. The precipitate is isolated by filtration, washed with 50 ml of n-hexane and thereafter dried under vacuum over $P_4O_{10}$/KOH. The product obtained is 5'-dimethoxytritylthymidine (5'-dimethoxytritylthymidine: 131 mg, 99% of dry solids with 100% internucleotide coupling in the synthesizer).

EXAMPLE 3

Preparation of 2-isobutyryl-5'-dimethoxytrityl-2'-desoxyguanosine from 2-i-butyryl-5'-dimethoxytrityl-2'-desoxyguanosin-3'-yl-β-cyanoethylphosphorodiisopropylamidite 350 mg (5 mmol) of tetrazole and 18 μl (1 mmol) of water are are added to a solution of 839 mg (1 mmol) of 2-isobutyryl-5'-dimethoxytrityl-2'-desoxyguanosin-3'-yl-βcyanoethylphosphorodiisopropylamidite in 8 ml of acetonitrile. After 5 minutes the hydrolysis of the phosphoroamidite is complete and 5'-dimethoxytritylguanosin-3'-cyanoethylhydrogenphosphonate is obtained.

To this solution are added 4 ml of methanol and 350 mg of imidazole. After 24 hours the reaction solution is concentrated by evaporation under vacuum, giving a white to yellowis solid, which is taken up in 50 ml of dichloromethane.

After extractions with 50 ml of water and 50 ml of sodium hydrogencarbonate, the organic phase is dried over sodium sulfate. The salt and any residual imidazole are removed by filtration. The crude product is concentrated by evaporation and separated by flash chromatography. The product fractions are combined and concentrated. The concentrate is taken up in 50 ml of dichloromethane and extracted with 50 ml of 1M of triethylammonium hydrogencarbonate. The organic phase is dried over sodium sulfate. The salt is removed by filtration and concentrated to a volume of 1 ml under vacuum. The concentrated product solution is precipitated at room temperature in 50 ml of n-pentane. The precipitation is brought to completion by addition of 450 ml of n-pentane and subsequent cooling to −20° C. The precipitate is isolated by filtration, washed with 100 ml of n-pentane and vacuum dried over $P_4O_{10}$/KOH. The product obtained is 2-isobutyryl-5'-dimethoxytrityl-2'-desoxyguanosine (2-i-butyryl-5'-dimethoxytrityl-2'-desoxyguanosine: 577 mg, 90.3% of dry solids).

EXAMPLE 4

Preparation of 6-benzoyl-5'-dimethoxytrityl-2'-desoxyadenosine from 6-benzoyl-5'-dimethoxytrityl-2'-desoxyadenosin-3'-yl-β-cyanoethylphosphorodiisopropylamidite 350 mg (5 mmol) of tetrazole and 18 μl (1 mmol) of water are are added to a solution of 857 mg (1 mmol) of 6-benzoyl-5'-dimethoxytrityl-2'-desoxyadenosin-3'-yl-β-cyanoethyl phosphorodiisopropylamidite in 8 ml of acetonitrile. After 5 minutes the hydrolysis of the phosphoroamidite is complete and 5'-dimethoxytrityladenosine-3'-cyanoethyl-hydrogenphosphonate is obtained.

To this solution are added 4 ml of methanol and 350 mg of imidazole. After 24 hours the reaction solution is concentrated by evaporation under vacuum, giving a white to yellowish solid, which is taken up in 50 ml of dichloromethane.

After extractions with 50 ml of water and 50 ml of sodium hydrogencarbonate, the organic phase is dried over sodium sulfate. The salt and any residual imidazole are removed by filtration. The crude product is concentrated by evaporation and separated by flash chromatography. The product fractions are combined and concentrated. The concentrate is taken up in 50 ml of dichloromethane and extracted with 50 ml of 1M of triethylammonium hydrogencarbonate. The organic phase is dried over sodium sulfate. The salt is removed by filtration and concentrated to a volume of 1 ml under vacuum. The concentrated product solution is precipitated at room temperature in 50 ml of n-pentane. The precipitation is brought to completion by addition of 450 ml of n-pentane and subsequent cooling to −20° C. The precipitate is isolated by filtration, washed with 100 ml of n-pentane and vacuum dried over $P_4O_{10}$/KOH. The product obtained is 6-benzoyl-5'-dimethoxytrityl-2'-desoxyadenosine-(6-benzoyl-5'-dimethoxytrityl-2'-desoxyadenosine: 562 mg, 85.5% of dry solids).

EXAMPLE 5

Preparation of 6-benzoyl-5'-dimethoxytrityl-2'-desoxyadenosine from 6-benzoyl-5'-dimethoxytrityl-2'-desoxyadenosine from the waste solution from an oligonucleotide synthesis reactor 300 ml of a waste solution formed in the reactor in the course of a DNA synthesis and containing 0.82 mmol of 6-benzoyl-5'-dimethoxytrityl-2'-desoxyadenosin-3'-yl-β-cyanoethylphosphonate are run into 50 ml of a solution of 1 g of imidazole in methanol. Upon conclusion of the reaction, the reaction solution is dried under vacuum to give a white to yellowish solid, which is taken up in 100 ml of dichloromethane. After extraction with 3×100 ml of 1M $NaH_2PO_4$/$NaHPO_4$, pH 5.5, the combined aqueous phase is extracted with 50 ml of dichloromethane. The organic phases are combined and then extracted with 2×100 ml of a saturated aqueous solution of sodium hydrogencarbonate. The sodium hydrogencarbonate phase is extracted with 50 ml of dichloromethane and all the organic phases are combined. The combined organic phase is dried over sodium sulfate. The crude product is concentrated by evaporation and separated by flash chromatography. The product fractions are combined and concentrated, then taken up in 50 ml of dichloromethane and extracted with 50 ml of 1M triethylammonium hydrogencarbonate. The organic phase is dried over sodium sulfate. The salt is removed by filtration and concentrated to a volume of 1 ml under vacuum. The concentrated product solution is precipitated at room temperature in 50 ml of n-pentane. The precipitation is brought to completion by addition of 200 ml of n-pentane and subsequent cooling to −20° C. The precipitate is isolated by filtration, washed with 50 ml of n-pentane and vacuum dried over $P_4O_{10}$/KOH. The product obtained is 6-benzoyl-5'-dimethoxytrityl-2'-desoxyadenosine (6-benzoyl-5'-dimethoxytrityl-2'-desoxyadenosine: 380 mg, 75.5% of dry solids with 100% internucleotide coupling in the synthesizer).

EXAMPLE 6

Preparation of 4-benzoyl-5'-dimethoxytrityl-2'-desoxycytidine from 4-benzoyl-5'-dimethoxytrityl-2'-desoxycytidin-3'-yl-β-cyanoethylphosphorodiisopropylamidite.

350 mg (5 mmol) of tetrazole and 18 μl (1 mmol) of water are added to a solution of 833 mg (1 mmol) of 4-benzoyl-5'-dimethoxytrityl-2'-desoxycytidine-3'-yl-β--cyanoethylphosphorodiisopropylamidite in 8 ml of acetonitrile. After 5 minutes the hydrolysis of the phosphoroamidite is complete and 5'-dimethoxytritylcytidine-3'-cyanoethyl-hydrogenphosphonate is obtained.

To this solution are added 4 ml of methanol and 350 mg of imidazole. After 24 hours the reaction solution is concentrated by evaporation under vacuum, giving a white to yellowish, solid which is taken up in 50 ml of dichloromethane.

After extractions with 50 ml of water and 50 ml of sodium hydrogencarbonate, the organic phase is dried over sodium sulfate. The salt and any residual imidazole are removed by filtration. The crude product is concentrated by evaporation and separated by flash chromatography. The product fractions are combined and concentrated. The concentrate is taken up in 50 ml of dichloromethane and extracted with 50 ml of 1M triethylammonium hydrogencarbonate. The organic phase is dried over sodium sulfate. The salt is removed by filtration and concentrated to a volume of 1 ml under vacuum. The concentrated product solution is precipitated at room temperature in 50 ml of n-pentane. The precipitation is brought to completion by addition of 450 ml of n-pentane and subsequent cooling to −20° C. The precipitate is isolated by filtration, washed with 100 ml of n-pentane and vacuum dried over $P_4O_{10}$/KOH. The product obtained is 4-benzoyl-5'-dimethoxytrityl-2'-desoxycytidine-(4-benzoyl-5'-dimethoxytrityl-2'-desoxycytidine: 527 mg, 83.2% of dry solids).

EXAMPLE 7

Preparation of 4-benzoyl-5'-dimethoxytrityl-2'-desoxycytidine from the waste solution from an oligonucelotide synthesis reactor 100 ml of a waste solution formed in the reactor in the course of a DNA synthesis and containing 0.27 mmol of 4-benzoyl-5'-dimethoxytrityl-2'-desoxycytidine-3'-yl-β-cyanoethylphosphonate are run into 50 ml of a solution of 1 g of imidazole in methanol. Upon conclusion of the reaction, the reaction solution is dried under vacuum to give a white to yellowish solid which is taken up in 100 ml of dichloromethane. After extraction with 3×100 ml of 1M $NaH_2PO_4$/$NaHPO_4$, pH 5.5, the combined aqueous phase is extracted with 50 ml of dichloromethane. The organic phases are combined and then extracted with 2×100 ml of a saturated aqueous solution of sodium hydrogencarbonate. The sodium hydrogencarbonate phase is extracted with 50 ml of dichloromethane and all the organic phases are combined. The combined organic phase is dried over sodium sulfate. The crude product is concentrated by evaporation and separated by flash chromatography. The product fractions are combined and concentrated. The concentrate is taken up in 50 ml of dichloromethane and extracted with 50 ml of 1M of triethylammonium hydrogencarbonate. The organic phase is dried over sodium sulfate. The salt is removed by filtration and concentrated to a volume of 1 ml under vacuum. The concentrated product solution is precipitated at room temperature in 50 ml of n-pentane. The precipitation is brought to completion by addition of 200 ml of n-pentane and subsequent cooling to −20° C. The precipitate is isolated by filtration, washed with 50 ml of n-pentane and vacuum dried over $P_4O_{10}$/KOH. The product obtained is 4-benzoyl-5'-dimethoxytrityl-2'-desoxycytidine (4-benzoyl-5'-dimethoxytrityl-2'-desoxycytidine: 163 mg, 91.5% of dry solids with 100% internucleotide coupling in the synthesizer).

EXAMPLE 8

Preparation of
N-methyl,N-(5'-dimethoxytrityl-3'-deoxythymid-3'-yl)-(5'-deoxythymid-5'-yl)acetamide from the waste solution from an oligonucelotide synthesis 5 ml of a waste solution formed in the reactor in the course of a DNA synthesis and containing 160 mg of N-methyl,N-(5'-dimethoxytrityl-3'-deoxythymid-3'-yl)-(3'cyanoethyl-H-phosphonyl-5'-deoxythymid-5'-yl)acetamide are run into 50 ml of a solution of 1 g of imidazole in methanol. The reaction is allowed to run for 3 days at 20°–25° C. The reaction mixture is diluted with 5 ml of water. Then a solution of 30 g of iodine, 20 ml of water, 200 ml of pyridine and 750 ml of tetrahydrofuran is added to the reaction mixture in an amount such that the brown iodine colour remains for at least 5 minutes. The reaction mixture is then concentrated by evaporation under vacuum to a yellowish solid, which is taken up in an emulsion consisting of 100 ml of 40% aqueous $NaHSO_3$ and 50 ml of ethyl acetate. The aqueous phase is separated and the organic phase is extracted again with $2 \times 50$ ml of an aqueous solution of sodium hydrogencarbonate. The aqueous phases are combined and extracted once more with 10 ml of ethyl acetate. The organic phases are combined, extracted with $2 \times 50$ ml of 50 ml of 1M aqueous $MgSO_4$ and then dried over 2 g of dry sodium sulfate. The salt is removed by filtration and the filtrate is concentrated to dryness under vacuum. The solid is taken up in 5 ml of $CH-Cl_3$/methanol(9:1) and the solution is chromatographed over a silica gel column. The product fractions are combined and dried under a high vacuum. The product, N-methyl,N-(5'-dimethoxytrityl-3'-deoxythymid-3'-yl)-(5'-deoxythymid-5'-yl)acetamide, precipitates in the form of a white foam in a yield of 40 mg (31% of theory).

$^1$H-NMR: ($CDCl_3$, standard=TMS, d[ppm]): 8.8: 2s, NH; 7,7: s, 1H, H$^6$; 7.45–7.2: DMTr; 7.09: s, 1H, H$^6$; 6.82: m, 4H, DMTr; 6.33: t, 1H, 1'; 6.15: t,1H, 1'; 5.26, 4,95: m, 1H, 3' at NRCH$_3$, 2 rotamers 3:1; 4,25–4: m, 2H; 3,75: s, 6H, DMTr; 3.63, 3.4, 3,25: 3m, 4H; 2.9, 2,85: 2s, 3H, CH$_3$ of NRCH$_3$, 2 rotamers: 3:1; 2.65–2: m; 1.88: 2H, 1.8: 1H, 2s, CH$_3^5$, 2 rotamers: 3:1; 1.5: 1H, 1.45: 2H, 2s, CH$_3^5$, 2 rotamers: 1:3.

EXAMPLE 9

Preparation of
5'-dimethoxytrityl-N$^6$-pivaloyl-2'-(-1-(2-fluorophenyl)-4-methoxypiperid-4-yl)-adenosine from the waste solution from an oligonucelotide synthesis reactor 5 ml of a waste solution formed in the reactor in the course of a DNA synthesis and containing 160 mg of N-methyl-N-(5'-dimethoxytrityl-3'-deoxythymid-3'-yl)-(3'cyanoethyl-H-phosphonyl-5'-deoxythymid-5'-yl)acetamide are run into 50 ml of a solution of 1 g of imidazole in methanol. The reaction is allowed to run for 3 days at 20°–25° C. The reaction mixture is diluted with 5 ml of water. Then a solution of 30 g of iodine, 20 ml of water, 200 ml of pyridine and 750 ml of tetrahydrofuran is added to the reaction mixture in an amount such that the brown iodine colour remains for at least 5 minutes. The reaction mixture is then concentrated by evaporation under vacuum to a yellowish solid, which is taken up in an emulsion consisting of 100 ml of 40% aqueous $NaHSO_3$ and 50 ml of ethyl acetate. The aqueous phase is separated and the organic phase is extracted again with $2 \times 50$ ml of an aqueous solution of sodium hydrogencarbonate. The aqueous phases are combined and extracted once more with 10 ml of ethyl acetate. The organic phases are combined, extracted with $2 \times 50$ ml of 50 ml of 1M aqueous $MgSO_4$ and then dried over 2 g of dry sodium sulfate. The salt is removed by filtration and the filtrate is concentrated to dryness under vacuum to give 320 g of crude product. The solid is taken up in 5 ml of $CH-Cl_3$/methanol(9:1) and the solution is chromatographed over a silica gel column. The product fractions are combined and dried under a high vacuum. The product, 5'-dimethoxytrityl-N$^6$-pivaloyl-2'(-1-(2-fluorophenyl)-4-methoxypiperid-4-yl)-adenosine, precipitates in the form of a yellow oil in a yield of 223 mg (58% of theory).

$^1$H-NMR: ($CDCl_3$, standard=TMS, d[ppm]): 8.69: s, 1H, adenine; 8.48: s, 1H, adenine; 8.2: s, 1H, adenine; 7.5–7.2: m, 9H, DMTr; 7,12–6,88: m, 4H, 2-Fluorophenyl; 6,83: 2m, 4H, DMTr; 6,25: d, 1H, 1'; 5.35: m; 4.43: m, 1H; 4.3: m, 1H; 3.76: s, 6H; 3.5, 3.38: 2m, 2H, 5'; 3.15: m, 1H, Fpmp; 2.96: m, 2H; Fpmp; 2.78: s, 3H, CH$_3$ of Fpmp, m, 1H, FPMP; 2.15–1.75: m, 4H, Fpmp; 1.4: 9H: piv.

EXAMPLE 10

Preparation of
5'-dimethoxytrityl-2'(-1-(2-fluorophenyl)-4-methoxypiperrid-4-yl)uridine from the hydrolysate of
5'-dimethoxytrityl-2'(-1-(2-fluorophenyl)-4-methoxypiperid-4-yl)uridine-3'-ylcyanoethylphosphorodiisopropylamidite; transesterification with methanol and KF, $I_2/H_2O$ as quench solution without $I_2$ acceptor in the working up 10 ml of a solution of 0.138 mmol of 5'-dimethoxytrityl-2-'(-1-(2-fluorophenyl)-4-methoxypiperid-4-yl)uridin-3'-yl-cyanoethyl-H-phosphonate and 0.694 mmol of tetrazole in acetonitrile are run into 50 ml of a 0.1M methanolic solution of KF. The reaction is complete within 2 days at 20°–25° C. The reaction mixture is diluted with 5 ml of water. Then a solution of 30 g of iodine, 20 ml of water, 200 ml of pyridine and 750 ml of tetrahydrofuran is added to the reaction mixture in an amount such that the brown iodine colour remains for at least 5 minutes. The reaction mixture is then concentrated by evaporation under vacuum to a yellowish solid, which is taken up in an emulsion consisting of 50 ml of water and 50 ml of ethyl acetate. The organic phases are combined and extracted again with $4 \times 50$ ml of water. The aqueous phases are combined and extracted once more with 10 ml of ethyl acetate. The organic phases are combined, extracted with 50 ml of a saturated solution of NaCl and then dried over 2 g of dry sodium sulfate. The salt is removed by filtration and the filtrate is concentrated. The solid is taken up in 5–10 ml of ethyl acetate and the solution is run slowly into 200 ml of n-pentane. The product falls out as a white amorphous precipitate. This precipitate is isolated by filtration, then washed with 50 ml of n-pentane, dried over $P_4O_{10}$/KOH for 24 hours under vacuum, giving 67.7 mg (69% of theory) of 5'-dimethoxytrityl-2'-(1-(2-fluorophenyl)-4-methoxypiperid-4-yl)uridine (75% of theory).

$^1$H-NMR: ($CDCl_3$, standard=TMS, d[ppm]): 7.75: d, 1H, H$^6$; 7.45–7.15: m, 9H, DMTr; 7.1–6.75: m, 4H, Fpmp, 2m, 4H, DMTr; 6.15: d, 1H, 1'; 5.2: d, 1H, H$^5$;

4.74: m, 1H, 2'; 4.3: m, 1H, 3'; 4,15: m, 1H, 4'; 3,76: s, 6H, DMTr; 3,38: m, 2H, 5'; 3.12: s, 3H, $CH_3$ of Fpmp; 3.2–2.8: m, 4H, Fpmp; 2.15–1.8: m, 4H.

EXAMPLE 11

Preparation of 5'-dimethoxytrityl-$N^4$-benzoyl-2'-(1-(2-fluorophenyl)-4-methoxypiperid-4-yl)cytidine from the hydrolysate of 5'-dimethoxytrityl-$N^4$-benzoyl-2'-(1-(2-fluorophenyl)-4-methoxypiperid-4-yl)cytidin-3'-ylcyanoetylphosphorodiisopropylamidite 10 ml of a solution of 0.129 mmol of 5'-dimethoxytrityl-$N^4$-benzoyl-2'-(1-(2-fluorophenyl)-4-methoxypiperid-4-yl)-cytidin-3'-ylcyanoethyl-H-phosphonate and 0.645 mmol of tetrazole in acetonitrile are run into 50 ml of a 0.1M methanolic solution of KF. The reaction is complete within 2 days at 20°–25° C. The reaction mixture is diluted with 5 ml of water. Then a solution of 30 g of iodine, 20 ml of water, 200 ml of pyridine and 750 ml of tetrahydrofuran is added to the reaction mixture in an amount such that the brown iodine colour remains for at least 5 minutes. The reaction mixture is then concentrated by evaporation under vacuum to a yellowish solid, which is taken up in an emulsion consisting of 50 ml of water and 50 ml of ethyl acetate. The organic phases are combined and extracted again with 4×50 ml of water. The aqueous phases are combined and extracted once more with 10 ml of ethyl acetate. The organic phases are combined, extracted with 50 ml of a saturated solution of NaCl and then dried over 2 g of dry sodium sulfate. The salt is removed by filtration and the filtrate is concentrated. The solid is taken up in 5–10 ml of ethyl acetate and the solution is run slowly into 200 ml of n-pentane. The product falls out as a white amorphous precipitate. This precipitate is isolated by filtration, then washed with 50 ml of n-pentane, dried over $P_4O_{10}$/KOH for 24 hours under vacuum, giving 83 mg (69% of theory) of 5'-dimethoxytrityl-$N^4$-benzoyl-2'-(1-(2-fluorophenyl)-4-methoxypiperid-4-yl)cytidine (80% of theory).

$^1$H-NMR: ($CDCl_3$, standard=TMS, d[ppm]): 8.28: d, 1H; 7.82: d, 2H, Bz; 7.6–7.23: m, 14H, Bz, DMTr, C; 7.03–6.77: d, 4H, DMTr, 2d, 4H, Fpmp; 4.66: t, 1H, 1'; 4.38: t, 1H, 2'; 4.17: m, 1H, 3', 3.74: s, 6H, DMTr; 3.48: m, 2H, 5'; 3.25–2.85: s, 3H, $CH_3$, Fpmp, m, 4H, Fpmp; 2.18–1.95: m, 4H, Fpmp. $^{19}$F-NMR: ($CDCl_3$, standard=TFA, d[ppm]): −123.5.

EXAMPLE 12

Preparation of 5'-dimethoxytrityl-$N^4$-(4-tert-butylphenoxyacetyl)-2'-deoxycytidine from the hydrolysate of 5'-dimethoxytrityl-$N^4$-(4-tert-butylphenoxyacetyl)-2'-deoxycytidin-3'-ylcyanoethylphosphorodiisopropylamidite 4 ml of a solution in acetonitrile which contains 200 mg of 5'-dimethoxytrityl-$N^4$-(4-tert-butylphenoxyacetyl)-2'-deoxycytidine from the hydrolysate of 5'-dimethoxytrityl-$N^4$-(4-tert-butylphenoxyacetyl)-2'-deoxycytidin-3'-ylcyanoethyl-H-phosphonate and 2 mmol of tetrazole are run into 40 ml of a 0.2M methanolic solution of KF. The dephosphitylation is complete within 4 hours at 20°–25° C. To the reaction mixture is then added 1 ml of pyridine, followed by the addition of 50 mg of sulfur. The reaction mixture is stirred for 60 minutes at 20°–25° C., filtered, then poured into 100 ml of ice-water. The resulting emulsion is extracted with 3×30 ml of ethyl acetate. The organic phases are combined, extracted with 50 ml of a saturated solution of NaCl, and then dried over 2 g of dry sodium sulfate. The salt is removed by filtration and the filtrate is concentrated to dryness under vacuum. The solid is taken up in 10 ml of ethyl acetate and the solution is run slowly into 300 ml of n-hexane. The product falls out as a white amorphous precipitate. This precipitate is isolated by filtration, then washed with 50 ml of n-pentane, dried over $P_4O_{10}$/KOH for 24 hours under vacuum, giving 112.8 mg (72.1% of theory) of 5'-dimethoxytrityl-$N^4$-(4-tert-butylphenoxyacetyl)-2'-deoxycytidine.

EXAMPLE 13

Transesterification with imidazole, quencher with $I_2$/water, working up with citrate buffer: Preparation of 5'-dimethoxytrityl-(3-N-trifluoroacetylaminopropyl)-2'-deoxyuridine from the waste solution from an oligonucleotide synthesis reactor 5 ml of a waste solution formed in the reactor in the course of a DNA synthesis and containing 120 mg of 5'-dimethoxytrityl-(3-N-trifluoroacetylaminopropyl)-2'-deoxyuridin-3'-ylcyanoethyl-H-phosphonate are run into 80 ml of a solution of 1 g of imidazole per 50 ml of methanol. The reaction is allowed to run for 3 days at 20°–25° C. The reaction mixture is diluted with 8 ml of water. Then a solution of 30 g of iodine, 20 ml of water, 200 ml of pyridine and 750 ml of tetrahydrofuran is added to the reaction mixture in an amount such that the brown iodine colour remains for at least 5 minutes. The reaction mixture is then concentrated by evaporation under vacuum to a yellowish solid, which is taken up in an emulsion consisting of 50 ml of pH:3–4 buffer and 40 ml of ethyl acetate. The buffer consists of 24 g of NaOH, 117 g of citric acid and 35 g of sodium chloride per liter of aqueous solution. The aqueous phase containing imidazole is separated and the organic phase is extracted again with 2×50 ml of buffer solution. The organic phase is then extracted with a saturated aqueous solution of sodium hydrogencarbonate and thereafter with 50 ml of a saturated solution of sodium chloride. The organic phase is dried over 2 g of dry sodium sulfate. The salt is removed by filtration and the filtrate is concentrated. The solid is taken up in 5–10 ml of ethyl acetate and the solution is run slowly into 250 ml of n-pentane. The product falls out as a white amorphous precipitate. This precipitate is isolated by filtration, then washed with 50 ml of n-pentane, dried over $P_4O_{10}$/KOH for 24 hours under vacuum, giving 80 mg (86% of theory) of 5'-dimethoxytrityl-(3-nitrofluoroacetylaminopropyl)-2'-deoxyuridine.

$^1$H-NMR($CDCl_3$, standard=TMS, [ppm]): 7.45–6.9: m, 9H, DMTr; 6.73: 2m, 4H, DMTr; 6.48: t, 1H, 1'; 4.56: m, 1H, 3'; 4.04: m, 1H, 4'; 3.7: s, 6H, DMTr; 3.5–3.4: 2m, 3.35–3.25: 2m, 2H, 5'; 2.97: s, 2H, $NH_2$; 2.47–2.37 m, 1H, 2'; 2,35–2.2 m, 1H, 2'; 1.82, m, 1H; 1.6,m, 1H; 1.45–1.15, m, 4H, aminopropyl.

EXAMPLE 14

Preparation of 5'-dimethoxytrityl-(propyn-1-yl)-2'-deoxyuridine from the waste solution from an oligonucleotide synthesis reactor 5 ml of a waste solution formed in the reactor in the course of a DNA synthesis and containing 250 mg of 5'-dimethoxytrityl-(propyn-1-yl)-2'-deoxyuridin-2'-deoxyuridin-3'-ylcyanoethyl-H-phosphonate are run into 67 ml of a solution of 1 g of imidazole per 50 ml of methanol. The reaction is allowed to run for 3 days at 20°-25° C. The reaction mixture is diluted with 8 ml of water. Then a solution of 30 g of iodine, 20 ml of water, 200 ml of pyridine and 750 ml of tetrahydrofuran is added to the reaction mixture in an amount such that the brown iodine colour remains for at least 5 minutes. The reaction mixture is then concentrated by evaporation under vacuum to a yellowish solid, which is taken up in an emulsion consisting of 50 ml of pH:3-4 buffer and 40 ml of ethyl acetate. The buffer consists of 24 g of NaOH, 117 g of citric acid and 35 g of sodium chloride per liter of aqueous solution. The aqueous phase containing imidazole is separated and the organic phase is extracted again with 2×50 ml of buffer solution. The organic phase is then extracted with a saturated aqueous solution of sodium hydrogencarbonate and thereafter with 50 ml of a saturated solution of sodium chloride. The organic phase is dried over 2 g of dry sodium sulfate. The salt is removed by filtration and the filtrate is concentrated. The solid is taken up in 5-10 ml of ethyl acetate and the solution is run slowly into 250 ml of n-pentane. The product falls out as a white amorphous precipitate. This precipitate is isolated by filtration, then washed with 50 ml of n-pentane, dried over $P_4O_{10}$/KOH for 24 hours under vacuum, giving 125 mg (68% of theory) of 5'-dimethoxytrityl-(propyn-1-yl)-2'-deoxyuridine.

$^1$H-NMR(CDCl$_3$, standard=TMS, d[ppm]): 7.95: s, 1H, NH; 7.4-7.15: m, 10H, DMTr; 6.78: 2s, 4H, DMTr; 6.24: t, 1H, 1'; 4.5: m, 3'; 4.06: m, 4'; 3.73: s, 6H, DMTr, 3,28: m, 2H, 5'; 2.43: m, 1H, 2'; 2.22: m, 1H, 2'; 1.61: s, 3H, CH$_3$ of propynyl.

EXAMPLE 15

Preparation of 5'-dimethoxytrityl-(3-trifluoroaminopropyn-1-yl)-2'-deoxyuridine from the waste solution from an oligonucleotide synthesis reactor 5 ml of a waste solution formed in the reactor in the course of a DNA synthesis and containing 200 mg of 5'-dimethoxytrityl-(3-aminopropyn-1-yl)-2'-deoxyuridine-2'-deoxyuridin-3'-yl-cyanoethyl-H-phosphonate are run into 78 ml of a solution of 1 g of imidazole 1 g of imidazole per 50 ml of methanol. The reaction is allowed to run for 3 days at 20°-25° C. The reaction mixture is diluted with 7.8 ml of water. Then a solution of 30 g of iodine, 20 ml of water, 200 ml of pyridine and 750 ml of tetrahydrofuran is added to the reaction mixture in an amount such that the brown iodine colour remains for at least 5 minutes. The reaction mixture is then concentrated by evaporation under vacuum to a yellowish solid, which is taken up in an emulsion consisting of 50 ml of pH:3-4 buffer and 40 ml of ethyl acetate. The buffer consists of 24 g of NaOH, 117 g of citric acid and 35 g of sodium chloride per liter of aqueous solution. The aqueous phase containing imidazole is separated and the organic phase is extracted again with 2×50 ml of buffer solution. The organic phase is then extracted with a saturated aqueous solution of sodium hydrogencarbonate and thereafter with 50 ml of a saturated solution of sodium chloride. The organic phase is dried over 2 g of dry sodium sulfate. The salt is removed by filtration and the filtrate is concentrated. The solid is taken up in 5-10 ml of ethyl acetate and the solution is run slowly into 250 ml of n-pentane. The product falls out as a white amorphous precipitate. This precipitate is isolated by filtration, then washed with 50 ml of n-pentane, dried over $P_4O_{10}$/KOH for 24 hours under vacuum, giving 113 mg (73% of theory) of 5'-dimethoxytrityl-(3-trifluoroacetylaminopropyn-1-yl)-2'-deoxyuridine.

$^1$H-NMR(CDCl$_3$, standard=TMS, d[ppm]): 8.15: s, 1H, NH; 7.4-7.15: 10H, DMTr, H$^6$; 6.26: t, 1H, 1'; 4.53: m, 1H, 3'; 3.97: m, 2H, 5'; 3.73: s, 6H, DMTr; 3.3: m, 2H, CH$_2$ von propynyl; 2.48, m, 1H, 2'; 2.25: m, 1H, 2'.

EXAMPLE 16

Preparation of N-5'-dimethoxytrityl-3'-deoxythymidin-3'-yl,N-propyl-3'-deoxythymid-5'-yl)acetamide from the waste solution from an oligonucleotide synthesis reactor 5 ml of a waste solution formed in the reactor in the course of a DNA synthesis and containing 200 mg of N-5'-dimethoxytrityl-3'-deoxythymidin-3'-yl-N-propyl-3'-deoxythymid-3'-cyano ethyl-H-phosphonyl-5'-yl)acetamide are run into 78 ml of a solution of 1 g of imidazole per 50 ml of methanol. The reaction is allowed to run for 7 days at 20°-25° C. The reaction mixture is diluted with 20 ml of water. Then a solution of 30 g of iodine, 20 ml of water, 200 ml of pyridine and 750 ml of tetrahydrofuran is added to the reaction mixture in an amount such that the brown iodine colour remains for at least 5 minutes. The reaction mixture is then concentrated by evaporation under vacuum to a yellowish solid, which is taken up in an emulsion consisting of 50 ml of pH:3-4 buffer and 40 ml of ethyl acetate. The buffer consists of 24 g of NaOH, 117 g of citric acid and 35 g of sodium chloride per liter of aqueous solution. The aqueous phase containing imidazole is separated and the organic phase is extracted again with 2×50 ml of buffer solution. The organic phase is then extracted with a saturated aqueous solution of sodium hydrogencarbonate and thereafter with 50 ml of a saturated solution of sodium chloride. The organic phase is dried over 2 g of dry sodium sulfate. The salt is removed by filtration and the filtrate is concentrated. The solid is taken up in 5-10 ml of ethyl acetate and the solution is run slowly into 600 ml of n-pentane. The product falls out as a white amorphous precipitate. This precipitate is isolated by filtration, then washed with 50 ml of n-pentane, dried over $P_4O_{10}$/KOH for 24 hours under vacuum, giving 107 mg (66% of theory) of N-5'-dimethoxytrityl-3'-deoxythymidin-3'-yl-N-propyl-3'-deoxythymid-5'-yl)-acetamide.

$^1$H-NMR(CDCl$_3$, standard=TMS, d[ppm]): $^1$H-NMR(CDCl$_3$, standard=TMS, d[ppm]): 7.65: s, 1H, H$^6$; 7.4-7.15: m, 9H, DMTr; 7.1: s, 1H, H$^6$; 6.77: 2s, 4H, DMTr; 6.53: t, 1H, 1'; 6.13: t, 1H, 1'; 4.28: m, 1H, 3'; 4.1: m, 2H, 3',4'; 3.72: s, 6H, DMTr, m, 1H; 3,52: m, 4', 1H; 3,5, d, 1H; 3,15-2,85: m, 3H, 5', CH$_2$ of acetamide; 2.56: m, 1H, 2'; 2.45-2.25: m, 3H, 2' CH$_2$ of propyl; 2.2-2.1: 2H, 2'; 1.83: s, 3H, CH$_3^5$; 1.45: s, 3H,CH$_3^5$; 1.22: m, 2H, CH$_2$ of propyl; 0.73: t, 3H, CH$_3$ of propyl.

EXAMPLE 17

Preparation of 5'-dimethoxytrityl-3'-propyl-5-methyluridine from the waste solution from an oligonucleotide synthesis reactor 5 ml of a waste solution formed in the reactor in the course of a DNA synthesis and containing 400 mg of 5'-dimethoxytrityl-3'-propyl-5-methyluridine-3'-cyano-ethyl-H-phosphonate are run into 100 ml of a solution of 1 g of imidazole per 50 ml of methanol. The reaction is allowed to run for 7 days at 20°-25° C. The reaction mixture is diluted with 20 ml of water. Then a solution of 30 g of iodine, 20 ml of water, 200 ml of pyridine and 750 ml of tetrahydrofuran is added to the reaction mixture in an amount such that the brown iodine colour remains for at least 5 minutes. The reaction mixture is then concentrated by evaporation under vacuum to a yellowish solid, which is taken up in an emulsion consisting of 50 ml of pH:3-4 buffer and 40 ml of ethyl acetate. The buffer consists of 24 g of NaOH, 117 g of citric acid and 35 g of sodium chloride per liter of aqueous solution. The aqueous phase containing imidazole is separated and the organic phase is extracted again with 2×50 ml of buffer solution. The organic phase is then extracted with a saturated aqueous solution of sodium hydrogencarbonate and thereafter with 50 ml of a saturated solution of sodium chloride. The organic phase is dried over 2 g of dry sodium sulfate. The salt is removed by filtration and the filtrate is concentrated to dryness. The residue is dried over $P_4O_{10}$/KOH for 24 hours under vacuum, giving 258 mg (86% of theory) of 5'-dimethoxytrityl-3'-propyl-5-methyluridine as a yellow oil.

$^1$H-NMR(CDCl$_3$, standard=TMS, d[ppm]): 8.45: s, 1H, NH; 7.57: s, 1H, H$^6$; 7.45-7.15: m, 9H, DMTr; 6.75:2s, 4H, DMTr; 5.9: d, 1H, 1'; 4.38: m, 1H, 3'; 4.0: m, 1H, 4'; 3.95: m, 1H, 2'; 3.72: s, 6H, DMTr.; 3.8-3.4: m, 2H: propyl; 3.6-3.3: 4m, 2H, 5'; 1.56: m, 2H, propyl; 1.88: t, 3H, propyl.

EXAMPLE 18

Transesterification of a phosphite on a polymer using methanol as acceptor alcohol 685 mg of a controlled pore glass (CPG) which is derivatised with thymidine-5'-cyanoeth-yl-H-phosphonate and is loaded with the nucleoside to a density of 36 mmol/g are reacted with 10 ml of a solution of 2% N-methylmorpholine in methanol. The nucleoside is covalently bonded through a succinyl group to its 3'-OH group with the CPG. After 1 hour, a sample of 137 mg of the solid phase is removed from the reaction mixture. The support is washed with 4×2 ml of acetonitrile and then reacted for 1 hour with 30 g of iodine, 20 ml of water, 200 ml of pyridine and 750 ml of tetrahydrofuran. The solid phase is thereafter washed with 10×2 ml of acetonitrile, and then with 10×2 ml of diethyl ether. The support is dried and treated at 55°-60° C. with a concentrated aqueous solution of ammonia. The solid phase, on which no more nucleoside is present, is removed by filtration. The filtrate is first lyophilised and then taken up in 0.1M triethylammonium acetate at pH7 and analysed by HPLC. A mixture of 5'-thymidinemonophosphate, thymidine and thymidine-5'-methylphosphate is detected. The thymidine-5'-phosphate is produced from the educt by iodooxidation and ammonolysis. The thymidine-5'-methylphosphate is produced from an intermediate of the dephosphitylation of the thymidine-5'-methyl-H-phosphonate in the course of the oxidative and hydrolytic working up. The thymidine is produced from the product of the dephosphitylation of the polymer-bonded thymidine after saponification of the succinyl group-linking group. The residual support is subjected for 36 hours to the aforementioned oxidative and ammonolytic working up. Solely thymidine is obtained in the filtrate of the support.

EXAMPLE 19

Transesterification of a phosphite on a polymer using cyanoethanol as acceptor alcohol 139 mg of a controlled pore glass (CPG) which is derivatised with thymidine-5'-cyanoethyl-H-phosphonate and loaded with the nucleoside to a density of 36 mmol/g are reacted with 10 ml of a solution of 10% N-methylmorpholine in cyanoethanol. The nucleoside is covalently bonded through a succinyl group to its 3'-OH group with the CPG. After 100 minutes the support is washed with 4×2 ml of acetonitrile and then reacted for 1 hour with 30 g of iodine, 20 ml of water, 200 ml of pyridine and 750 ml of tetrahydrofuran. The solid phase is thereafter washed with 10×2 ml of acetonitrile, and then with 10×2 ml of diethyl ether. The support is dried and treated at 55°-60° C. with a concentrated aqueous solution of ammonia. The solid phase, on which no more nucleoside is present, is removed by filtration. The filtrate is first lyophilised and then taken up in 0.1M triethylammonium acetate at pH 7 and analysed by HPLC. A mixture of 5'-thymidinemonophosphate and thymidine in the ratio 3:97 is detected. The thymidine-5'-phosphate is produced from the educt by iodooxidation and ammonolysis. The thymidine is produced from the product of the dephosphitylation of the polymer-bonded thymidine after saponification of the succinyl group-linking group.

EXAMPLE 20

Transesterification of a phosphite on a polymer using methanol as acceptor alcohl in the presence of magnesium ditrifluoroacetate Mg(OTf)$_2$ 139 mg of a controlled pore glass (CPG) which is derivatised with thymidine-5'-cyanoethyl-H-phosphonate and loaded with the nucleoside to a density of 36 mmol/g are reacted with 10 ml of a solution of 0.1M Mg(OTf)$_2$ in N-methylimidazole:methanol (1:9). The nucleoside is covalently bonded through a succinyl group to its 3'-OH group with the CPG. After 30 minutes, the support is washed with 4×2 ml of acetonitrile and then reacted for 1 hour with 30 g of iodine, 20 ml of water, 200 ml of pyridine and 750 ml of tetrahydrofuran. The solid phase is thereafter washed with 10×2 ml of acetonitrile, and then with 10×2 ml of diethyl ether. The support is dried and treated at 55°-60° C. with a concentrated aqueous solution of ammonia. The solid phase, on which no more nucleoside is present, is removed by filtration. The filtrate is first lyophilised and then taken up in 0.1M triethylammonium acetate at pH 7 and analysed by HPLC. A mixture of thymidine and thymidine-5'-methylphosphate is detected. The thymidine-5'-methylphosphate is produced from an intermediate of the dephosphitylation of thymidine-5'-methyl-H-phosphonate in the course of the iodooxidation and hydrolysis. The thymidine is produced from the product of the dephosphitylation of the polymer-bonded thymidine after saponification of the succinyl group-linking group. The ratio of thymidine to thymidine-5'-methylphosphate is 97:3.

EXAMPLE 21

Transesterification of a phosphite on a polymer using cyanoethanol as acceptor alcohol in the presence of LiCl 139 mg of a controlled pore glass (CPG) which is derivatised with thymidine-5'-cyanoethyl-H-phosphonate and is loaded with the nucleoside to a density of 36 mmol/g are reacted with 10 ml of a solution of 0.1M LiCl in N-methylmorpholine:cyanoethanol (1:9). The nucleoside is covalently bonded through a succinyl group to its 3'-OH group with the CPG. After 30 minutes, the support is washed with 4×2 ml of acetonitrile and then reacted for 1 hour with 30 g of iodine, 20 ml of water, 200 ml of pyridine and 750 ml of tetrahydrofuran. The solid phase is thereafter washed with 10×2 ml of acetonitrile, and then with 10×2 ml of diethyl ether. The support is dried and treated at 55°-60° C. with a concentrated aqueous solution of ammonia. The solid phase, on which no more nucleoside is present, is removed by filtration. The filtrate is first lyophilised and then taken up in 0.1M triethylammonium acetate at pH 7 and analysed by HPLC. A mixture of thymidine and thymidine-5'-phosphate is detected. The thymidine-5'-phosphate is produced from the educt by iodooxidation and ammonolysis. The thymidine is produced from the product of the dephosphitylation of the polymer-bonded thymidine after saponification of the succinyl group-linking group. The ratio of thymidine to thymidine-5'-phosphate is 98:2.

What is claimed is:

1. A process for the preparation of natural or synthetic nucleosides, nucleoside analogs or oligonucleotides from at least two such nucleosides and/or nucleoside analogs whose basic molecule contains an unsubstituted or substituted radical of a nucleic base B and a protected hydroxyl group of formula $R_1$—O—, wherein $R_1$ is a protective group, or which are linked to the oxygen atom of a hydroxyl group direct or to a solid support through a linking group, from nucleoside monomers or from oligonucleotides to the basic molecule of which, in addition to said radicals, a group of formula I, Ia or Ib

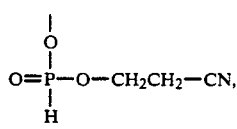

(I)

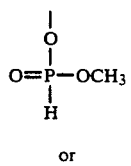

(Ia)

or

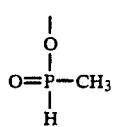

(Ib)

is attached, by converting the group of formula I, Ia or Ib into a hydroxyl group —OH by reacting the nucleosides or oligonucleotides, in the absence or presence of an inert organic solvent, with an excess of an aliphatic, cycloaliphatic araliphatic or aromatic alcohol containing 1 to 30 carbon atoms, a polyol containing 2 to 50 carbon atoms or a polymeric polyol, in the presence of at least a catalytic amount of an inorganic base or of an organic nitrogen base, which base has a pK value of 4 to 10.

2. A process according to claim 1, wherein the solvent is selected from the group consisting of ethers, halogenated hydrocarbons, carboxamides, lactams, sulfoxides, sulfones, aromatic hydrocarbons, nitriles, aliphatic and cycloaliphatic hydrocarbons.

3. A process according to claim 2, wherein the solvent is selected from the group consisting of ethers, halogenated hydrocarbons, nitriles, carboxamides and lactams.

4. A process according to claim 3, wherein the solvent is tetrahydrofuran or dioxane.

5. A process according to claim 2, wherein the solvent is selected from the group consisting of acetonitrile, propionitrile, benzonitrile and phenylacetonitrile.

6. A process according to claim 1, wherein the aliphatic, cycloaliphatic, araliphatic or aromatic alcohol, the polyol or the polymeric polyol is present is present in an excess of at least 100 molar equivalents and up to 1000 molar equivalents of hydroxyl groups per molar equivalent groups of formula I.

7. A process according to claim 1, wherein the reaction is carried out in the temperature range from −20° C. to +55° C.

8. A process according to claim 7, wherein the reaction is carried out in the temperature range from 15° C. to 35° C.

9. A process according to claim 8, wherein the reaction is carried out at room temperature.

10. A process according to claim 1, wherein the alcohol is an alkanol of 1 to 20 carbon atoms.

11. A process according to claim 10, wherein the alcohol is an alkanol of 1 to 12 carbon atoms.

12. A process according to claim 11, wherein the alcohol is an alkanol of 1 to 6 carbon atoms.

13. A process according to claim 10, wherein the alcohol is selected from the group consisting of methanol, ethanol, n- and isopropanol, n-, iso- and tert-butanol, pentanol, hexanol, ethylene glycol, diethylene glycol monomethyl and monoethylether.

14. A process according to claim 10, wherein the alcohol is an alkanol of 1 to 4 carbon atoms.

15. A process according to claim 14, wherein the alcohol is methanol.

16. A process according to claim 1, wherein the alcohol is a cycloalkanol of 5 to 12 carbon atoms.

17. A process according to claim 16, wherein the alcohol is a cycloalkanol of 5 to 8 carbon atoms.

18. A process according to claim 16, wherein the alcohol is selected from the group consisting of cyclopentanol, cyclohexanol, methylcyclohexanol, cycloheptanol and cyclooctanol.

19. A process according to claim 1, wherein the alcohol is an araliphatic alcohol of 7 to 30 carbon atoms.

20. A process according to claim 19, wherein the alcohol is an araliphatic alcohol of 7 to 20 carbon atoms.

21. A process according to claim 19, wherein the alcohol is selected from the group consisting of unsubstituted or alkyl- or alkoxy-substituted benzyl alcohol and β-phenylethanol.

22. A process according to claim 1, wherein the alcohol is an aromatic alcohol of 6 to 30 carbon atoms.

23. A process according to claim 19, wherein the alcohol is an aromatic alcohol of 6 to 12 carbon atoms.

24. A process according to claim 22, wherein the alcohol is selected from the group consisting of phenol, naphthol and unsubstituted and alkyl- or alkoxy-substituted phenol or naphthol.

25. A process according to claim 1, wherein the polyol contains 2 to 20 carbon atoms.

26. A process according to claim 25, wherein the polyol is selected from the group consisting of ethylene glycol, propylene glycol, butanediol, pentanediol, hexanediol, cyclohexanediol, dihydromethylcyclohexane, diethylene glycol, triethylene glycol, polyethylene glycol, trimethylolpropane, pentaerythritol, dipentaerythritol, glycerol and saccharides.

27. A process according to claim 1, wherein the polymeric polyol is selected from the group consisting of polyvinyl alcohol, polysaccharides and hydroxyalkyl polyacrylates and hydroxyalkyl polymethacrylates.

28. A process according to claim 1, wherein the inorganic base is selected from the group consisting of basic metal oxide, heavy metal oxide and hydroxide.

29. A process according to claim 28, wherein the inorganic base is basic alumina.

30. A process according to claim 28, wherein the inorganic base is basic silicondioxide.

31. A process according to claim 1, wherein the catalytic amount of base is in the range from 0.01 to 20% molar.

32. A process according to claim 1, wherein the organic nitrogen base is selected from the group consisting of aromatic amine, aromatic N-heterocycle and N-alkylmorpholine.

33. A process according to claim 32, wherein the base is selected from the group consisting of imidazole, pyridine, polyvinyl pyridine, N-methylmorpholine, aniline and o-diaminobenzene.

34. A process according to claim 1, wherein the nucleoside or the oligonucleotide is linked to a solid support.

35. A process according to claim 1, wherein additionally catalytic amounts of an inorganic base is used that catalyses the reaction nucleophically.

36. A process accoridng to claim 1, wherein calatytic amounts of a Lewis acid are additionally used.

* * * * *